(12) United States Patent
Feuerlein et al.

(10) Patent No.: US 8,687,762 B2
(45) Date of Patent: Apr. 1, 2014

(54) CT SYSTEM

(75) Inventors: Ute Feuerlein, Erlangen (DE); Stefan Käpplinger, Jena (DE)

(73) Assignee: Siemens Aktiengesellschaft, Munich (DE)

( * ) Notice: Subject to any disclaimer, the term of this patent is extended or adjusted under 35 U.S.C. 154(b) by 403 days.

(21) Appl. No.: 13/182,596

(22) Filed: Jul. 14, 2011

(65) Prior Publication Data

US 2012/0014499 A1 Jan. 19, 2012

(30) Foreign Application Priority Data

Jul. 16, 2010 (DE) .......................... 10 2010 027 311

(51) Int. Cl.
*G01N 23/083* (2006.01)
*H05G 1/60* (2006.01)

(52) U.S. Cl.
USPC .................................. 378/8; 378/95; 378/901

(58) Field of Classification Search
USPC ............. 378/4–20, 91, 95, 96–98, 98.5, 98.8, 378/145, 162, 165, 204, 207, 210, 901
See application file for complete search history.

(56) References Cited

U.S. PATENT DOCUMENTS

| | | | |
|---|---|---|---|
| 4,835,690 A | 5/1989 | Gangarosa et al. | |
| 5,687,208 A * | 11/1997 | Bae et al. ........................... | 378/8 |
| 7,639,782 B2 * | 12/2009 | Zelnik et al. ..................... | 378/62 |
| 7,835,497 B2 * | 11/2010 | Haras .............................. | 378/98 |
| 8,537,969 B2 * | 9/2013 | Allmendinger ................. | 378/62 |
| 2005/0065825 A1 | 3/2005 | Boing et al. | |
| 2006/0291614 A1 * | 12/2006 | Horiuchi et al. .................. | 378/4 |
| 2007/0081630 A1 | 4/2007 | Evron | |
| 2008/0292048 A1 * | 11/2008 | Haras et al. ..................... | 378/20 |
| 2010/0128838 A1 | 5/2010 | Ayala et al. | |

FOREIGN PATENT DOCUMENTS

| | | |
|---|---|---|
| CN | 101732060 | 6/2010 |
| DE | 10335119 A1 | 2/2005 |
| WO | WO 2005/051198 | 6/2005 |

OTHER PUBLICATIONS

Office Action for corresponding Chinese patent application No. 2011101979379 dated Aug. 24, 2012 with English translation.
German Office Action.

* cited by examiner

*Primary Examiner* — Anastasia Midkiff
(74) *Attorney, Agent, or Firm* — Harness, Dickey & Pierce, P.L.C.

(57) ABSTRACT

A CT system for scanning a patient is disclosed. In at least one embodiment, the system includes a tube/detector system, which can be set by a control device in respect of tube voltage and/or dose power; a patient couch, which can be displaced in a controlled fashion at least in the direction of a system axis; and a computer system, which can control the CT system. In at least one embodiment, the system includes an evaluation unit for a prescribed logical decision tree, which is integrated into the computer system, and which determines examination and scan parameters for the CT system on the basis of the input of at least one patient parameter described in a parameter list and operates the CT system using these examination and scan parameters.

12 Claims, 3 Drawing Sheets

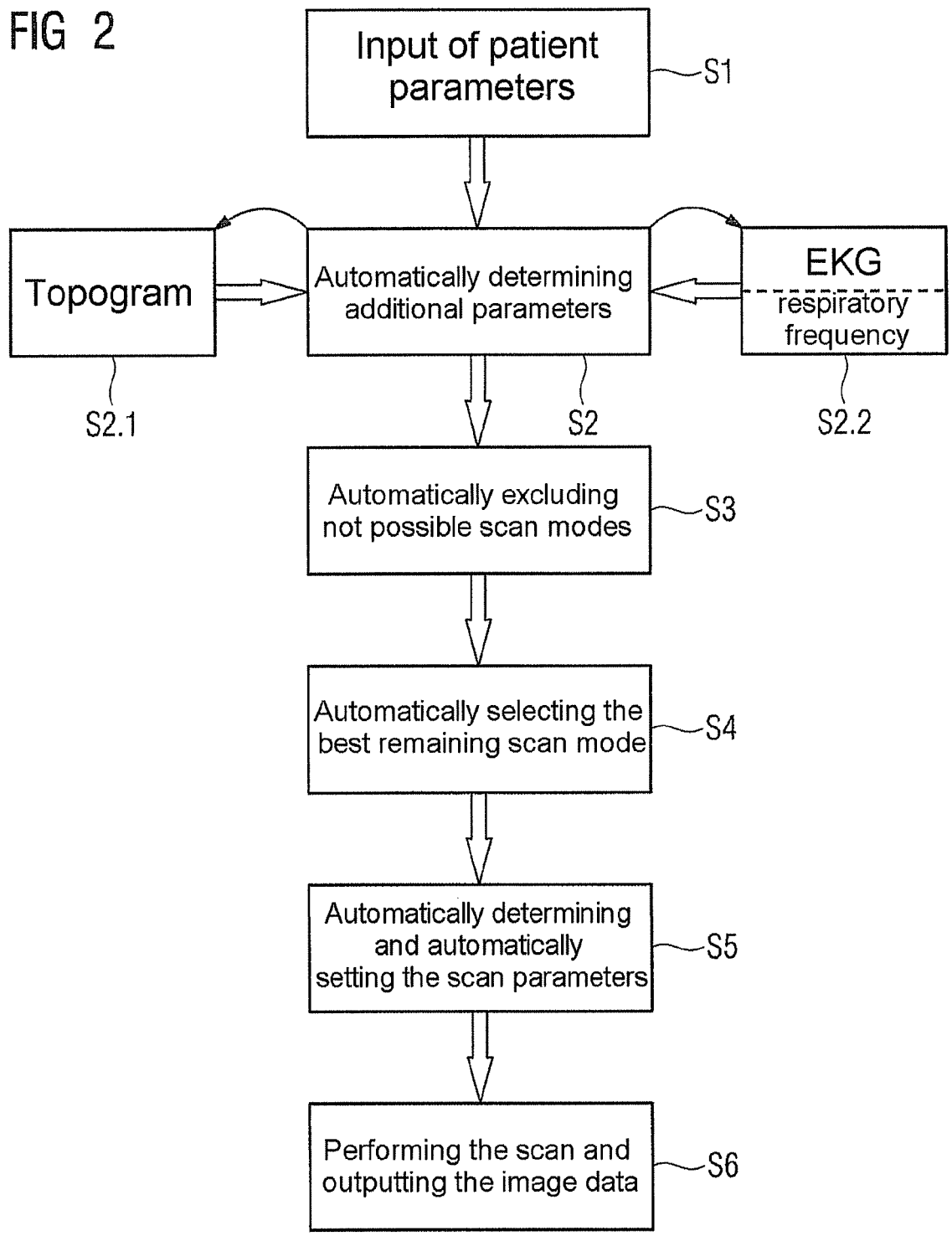

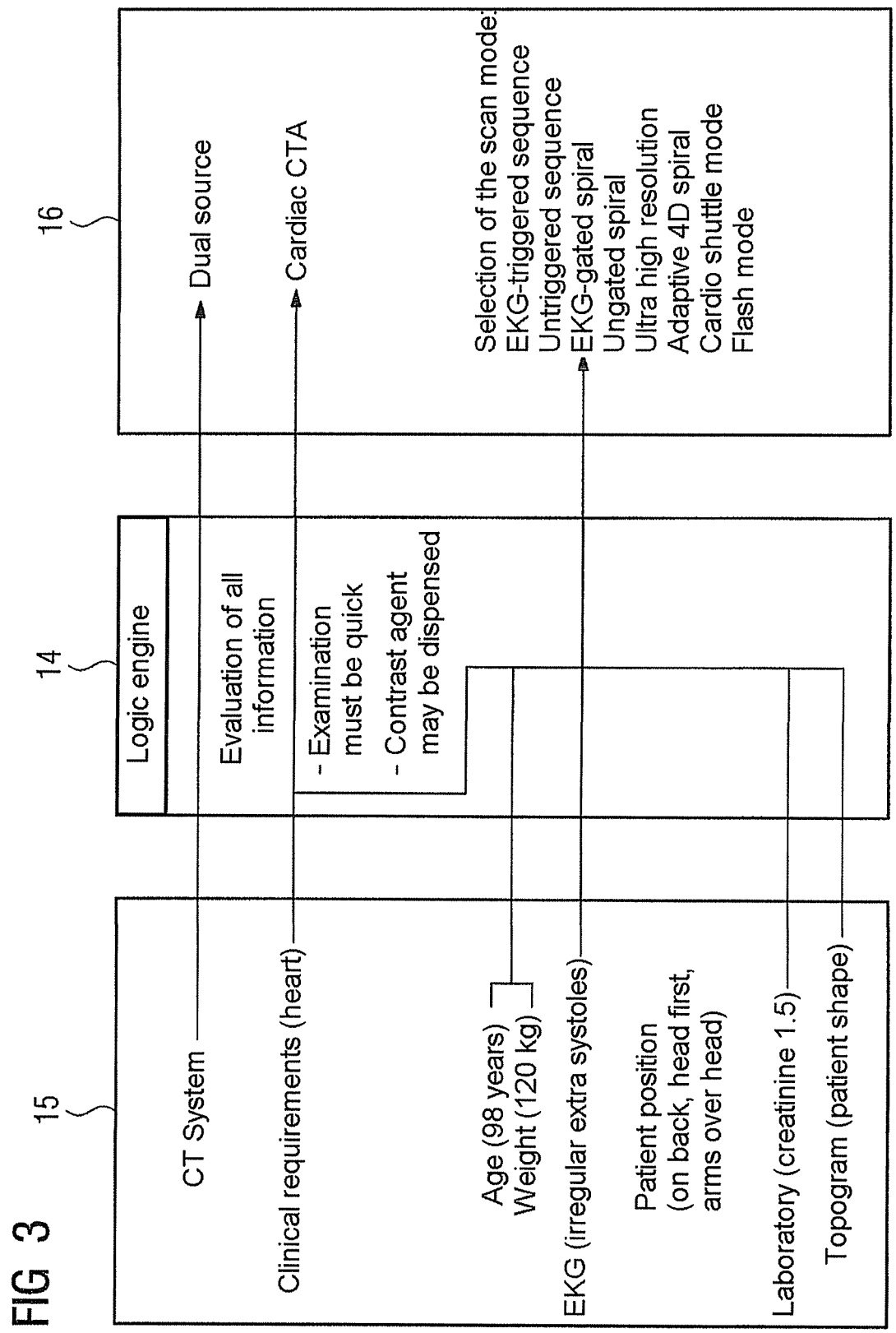

CT SYSTEM

PRIORITY STATEMENT

The present application hereby claims priority under 35 U.S.C. §119 on German patent application number DE 10 2010 027 311.2 filed Jul. 16, 2010, the entire contents of which are hereby incorporated herein by reference.

FIELD

At least one embodiment of the invention generally relates to a CT system for scanning a patient, at least comprising a tube/detector system, which can be set by a control device in respect of tube voltage and/or dose power, a patient couch, which can be displaced in a controlled fashion at least in the direction of a system axis, and/or a computer system, which can control the CT system.

BACKGROUND

CT systems of the above-described type are well known. In general, such CT systems comprise the option of selecting predefined scan protocols according to demand or independently defining their own scan protocols, wherein such scan protocols generally set the CT system such that it scans an "average" patient, wherein there additionally is the option of selecting specific organ systems that should be made clearly visible. Moreover, there is also the option of selecting between e.g. gated or ungated scan modes, in which the further settings in respect of the optimum advance and similar parameters are then determined automatically.

However, in principle, there is a problem with these settings both in the supplied scan protocols and in the individually programmed scan protocols, which only partly cover the entire complexity created during a patient-specific scan. A further problem lies in the fact that there are no control mechanisms that take into account possible incompatibilities of the patient in relation to the performed examination.

SUMMARY

In at least one embodiment of the invention, a CT system is disclosed, in which, depending on the specific patient and the specific clinical question, the optimum scan mode to be applied for this is selected automatically, including the boundary conditions necessary for this, and thereby excludes possible human error and, overall, makes the use of CT systems safer.

The inventors have recognized that it is possible to equip a CT system with an evaluation unit for a complex logical decision tree, which establishes the optimum mode for examining the patient and for solving the clinical question on the basis of prescribed patient-specific and examination-specific boundary conditions, possibly after carrying out an additional preliminary examination such as creating a topogram, and then automatically sets the CT system according to these identified parameters and possibly also automatically starts the examination.

In accordance with this basic idea, the inventors propose to improve a CT system for scanning a patient, at least comprising a tube/detector system, which can be set by a control device in respect of tube voltage and/or dose power, a patient couch, which can be displaced in a controlled fashion at least in the direction of a system axis, and which has a computer system, which can control the CT system to the effect that an evaluation unit for a prescribed logical decision tree, i.e. a logic engine, is integrated into the computer system, which evaluation unit determines examination and scan parameters for the CT system on the basis of the input of at least one patient parameter described in a parameter list and operates the CT system using these examination and scan parameters.

By way of example, the parameter list can contain at least one of the following patient parameters:
 organ to be examined,
 clinical question,
 individual characteristics of the patient (weight, height, age, sex),
 laboratory values of the patient, more particularly creatinine, and
 physiological values of the patient.

Moreover, the logical decision tree can be embodied such that a decision is made on the basis of the entered patient parameters as to whether a topogram is created and whether this is optionally generated automatically and utilized as a further patient parameter.

The logical decision tree can also be embodied such that at least one examination parameter from the following list is determined on the basis of the previously specified patient parameters, and signaled to the operating staff:
 position the patient is in,
 necessity and medical possibility of a contrast-agent application,
 necessity of applying an EKG, and
 necessity of measuring the respiration.

Here, the signaling can be effected both in a visual and an audible fashion.

Moreover, the inventors demand that at least one scan parameter from the following list is determined on the basis of the previously specified patient parameters and examination parameters, and applied:
 type of the scan with:
 single-source/dual-source,
 single-energy/dual-energy,
 continuous scanning,
 respiratory-controlled spiral scanning,
 respiratory-controlled sequence,
 CTA scan with:
  EKG-triggered sequence,
  EKG-triggered spiral,
  adaptive 4D spiral,
  cardio shuttle,
  flash mode,
 scanning with ultra high resolution,
 dose power,
 dose modulation, and
 tube voltage.

BRIEF DESCRIPTION OF THE DRAWINGS

In the following text, the invention will, on the basis of the example embodiments, be explained in more detail with the aid of the figures, with only the features required for the understanding of the invention being illustrated. The following reference signs are used: 1: CT system; 2: first X-ray tube; 3: first detector; 4: second X-ray tube; 5: second detector; 6: gantry housing; 7: patient; 8: patient couch; 9: system axis; 10: computer system; 11: contrast-agent injector; 12: EKG measurement line; 14: decision tree/logic engine; 15: parameter list; 16: examination and scan parameters; $Prg_1$-$Prg_n$: computer programs; S1=method step 1≙ input of patient parameters; S2=method step 2≙ automatically determining additional parameters in the CT system; S2.1=method step 2.1≙ generating a topogram; S2.2=method step 2.2≙ evaluating the EKG and/or the respiratory frequency; S3=method step 3≅ automatically excluding not possible scan modes; S4=method step 4≅ automatically selecting the best remaining scan mode; S5=method step 5≅ automatically determining and automatically setting the scan parameters; S6=method step 6≅ performing the scan and outputting the image data.

In detail:

FIG. 2 shows a flowchart for working through a decision tree according to an embodiment of the invention, and FIG. 3 shows a schematic illustration of the logic engine in the computer system of a CT system.

DETAILED DESCRIPTION OF THE EXAMPLE EMBODIMENTS

Figure 1:
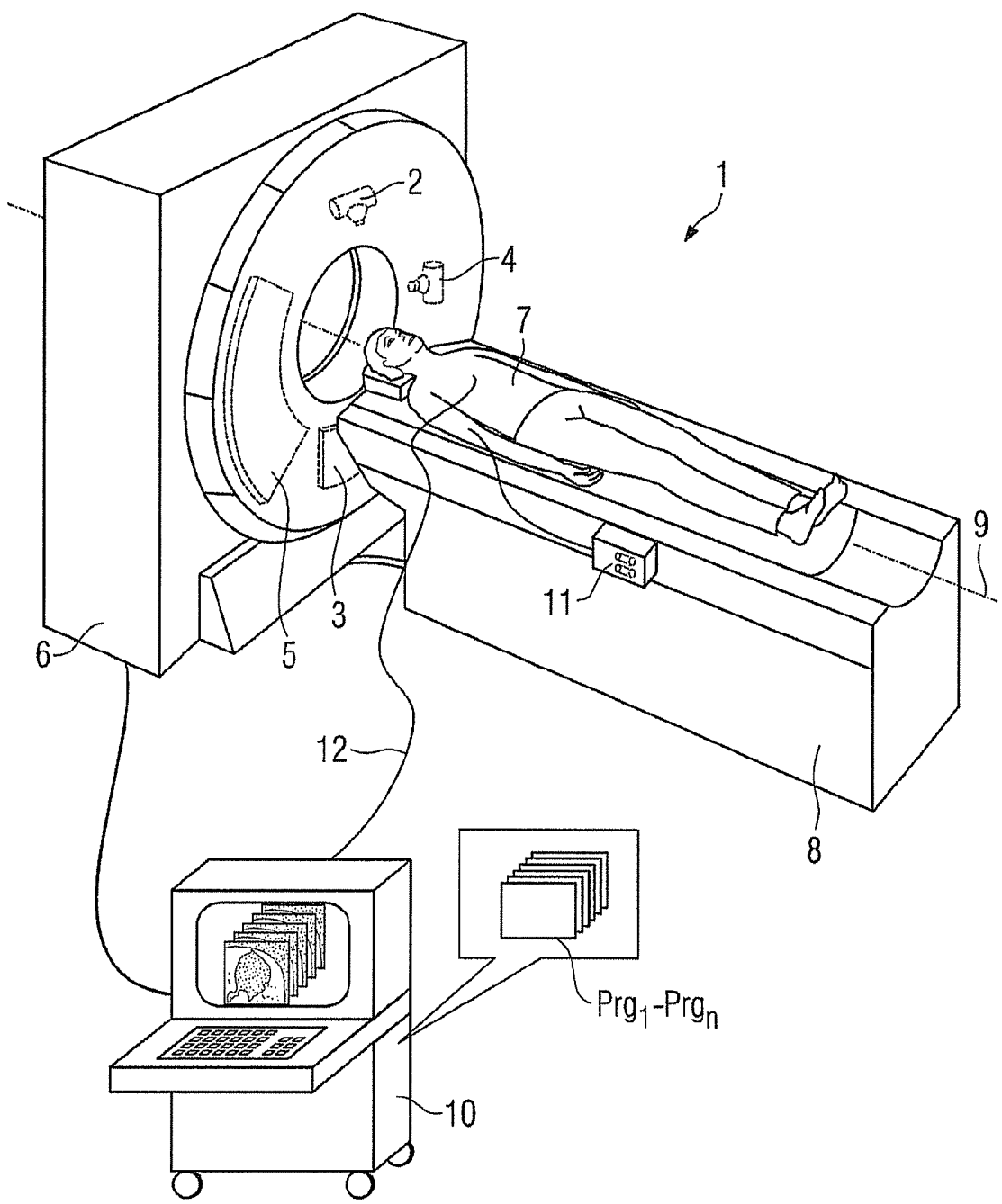
FIG. 1 shows a CT system according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein; the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example of a CT system 1 according to an embodiment of the invention, in which a patient 7, who is situated on a displaceable patient couch 8, is moved through an opening in the gantry housing 6 along the system axis 9, while the gantry (not illustrated in any more detail here) moves around the patient 7 in a rotating fashion. On the gantry there is at least one tube/detector system, which consists of a first X-ray tube 2 with an opposing detector 3. Optionally, a second tube/detector system with a second X-ray tube 4 and a second detector 5 may also be arranged on the same gantry. As a result of the continuous or sequential movement of the patient along the system axis 9, a spiral or sequentially circular scan of the patient takes place, which scan is controlled by a computer system 10, wherein the evaluation of the detector data and the final reconstruction can also be carried out by this computer system.

According to an embodiment of the invention, this computer system 10 also contains programs $Prg_1$ to $Prg_n$, which describe an evaluation unit with a prescribed logical decision tree. During the operation of the CT system 1, a multiplicity of examination and scan parameters are determined, according to an embodiment of the invention, for the CT system on the basis of the input of at least one patient parameter described in a parameter list and the CT system is operated using these examination and scan parameters. To this end, the CT system 1 is equipped with an additional contrast-agent injector 11, which can likewise be controlled by the computer system 10, and an EKG measurement line 12, which moreover allows the computer system 10 to perform a current scan of the EKG of the patient to be examined and, if necessary, to perform an EKG-gated cardiac examination.

FIG. 2 shows an example for the method procedure of such an examination with the aid of the logic engine according to the invention. In the process, a list with known patient parameters is firstly input in method step S1. Thereupon, additional parameters are automatically determined in the CT system during method step S2, wherein, depending on the input patient parameters a topogram may be triggered in method step S2.1 where necessary, the results of which in turn flow back into the logic engine. Alternatively, it is also possible for the EKG to be additionally recorded in method step S2.2 or for the respiratory frequency of the patient to be measured.

Once the sum of all parameters known about the patient is thereby present in the system, scan modes that cannot be performed are automatically excluded in method step S3. Thereupon, the best remaining scan mode that can be used to solve the clinical question is automatically selected from the remaining possible scan modes. Now there is an automatic determination and automatic setting of the scan parameters for the selected scan mode in method step S5 and finally, in method step S6, the scan is performed and the CT image data is output.

Reference is made to the fact that it goes without saying that there additionally is also the option for the operator of the CT system to be able to intervene manually in the automatically determined settings or the automatically determined scan mode. It may also be the case that it is not possible to select a specific scan mode unambiguously on the basis of the established patient parameters and examination parameters, and so a list of possible scan modes is output in the meantime and the operating staff can in this case make independent decisions as to which scan mode is preferred, wherein, subsequently, the automatic progress of the system continues in turn on the basis of the then selected scan mode and the optimum scan parameters are respectively set for this.

In practical terms, such a decision could appear as illustrated in FIG. 3. Here, the available information from the parameter list 15 is supplied from the left-hand side to the logic engine 14, which is symbolically illustrated as a box. After processing in the logic engine 14, the output information is gathered as examination and scan parameters 16 on the right-hand side. The procedure could then take place as outlined below:

The system is provided with very diverse data that leads to the selection of the optimum scan mode, for example:
CT system,
clinical demands, organ to be examined,
patient data such as age and weight,
laboratory data, such as creatinine value,
patient position,
physiological curves, and
topogram.

The system then selects the scan mode from this data, for example:
CT system=power, single/dual-source,
clinical demands, organ to be examined=cardiac CTA,
patient data such as age and weight=98 years, 200 kg,
laboratory data, such as creatinine value=1.5,
patient position=on back, head first, arms over head,
physiological curves=EKG for identifying the cardiac frequency and respiratory curve for setting the required breathe command, and
topogram=for calculating the dose.
Scan mode calculation:
dual-source system,
cardiac CTA→excludes EKG triggered sequence, standard sequence, standard spiral, dyn serio, multiscan, cardio shuttle, fluoroscopy, dual energy, ultra high resolution (UHR), respiratory-controlled spirals and sequences,
98 years, 200 kg→examination must be quick→excludes adaptive 4D spiral,
creatinine value=1.5→contrast-agent examination is possible,
on back, head first, arms over head→examination is possible,
EKG→irregular approximately 120 bpm→excludes Half-Beat cardio mode, and
topogram=for calculating the dose;
what remains is an EKG-gated spiral.

It is understood that the aforementioned features of the invention can be used not only in the respectively specified combination, but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that, are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A CT system for scanning a patient, comprising:
a tube/detector system, settable by a control device in respect of at least one of tube voltage and dose power;
a patient couch, displaceable in a controlled fashion at least in the direction of a system axis;
a computer system to control the CT system, the computer system including,
an evaluation unit for a logical decision tree, integrated into the computer system, to determine examination and scan parameters for the CT system on the basis of input of at least one patient parameter described in a parameter list and to operate the CT system using the determined examination and scan parameters, wherein the evaluation unit is configured to make a decision based on the entered patient parameters as to whether a topogram is created and determine whether to utilize the topogram as a further patient parameter.

2. The CT system as claimed in claim 1, wherein the parameter list contains at least one of the following patient parameters:
an organ to be examined,
a clinical question,
individual characteristics of the patient,
laboratory values of the patient, and
physiological values of the patient.

3. The CT system as claimed in claim 1, wherein the CT system is configured to determine at least one examination parameter from the following list on the basis of previously specified patient parameters, and signaled:
a position the patient is in,
a necessity and medical possibility of a contrast-agent application,
a necessity of applying an EKG, and
a necessity of measuring the respiration.

4. The CT system as claimed in claim 1, wherein the CT system is configured to determine at least one scan parameter from the following list on the basis of previously specified patient parameters and examination parameters, and applied:
a type of the scan with at least one of,
single-source/dual-source,
single-energy/dual-energy,
continuous scanning,
respiratory-controlled spiral scanning,
respiratory-controlled sequence,
CTA scan with at least one of
EKG-triggered sequence,
EKG-triggered spiral,
adaptive 4D spiral,
cardio shuttle, and
flash mode,
scanning with ultra high resolution,
dose power,
dose modulation, and
tube voltage.

5. The CT system as claimed in claim 2, wherein the CT system is configured to determine at least one examination parameter from the following list on the basis of previously specified patient parameters, and signaled:
a position the patient is in,
a necessity and medical possibility of a contrast-agent application,
a necessity of applying an EKG, and
a necessity of measuring the respiration.

6. The CT system as claimed in claim 2, wherein the CT system is configured to determine at least one scan parameter from the following list on the basis of previously specified patient parameters and examination parameters, and applied:
a type of the scan with at least one of,
single-source/dual-source,
single-energy/dual-energy,
continuous scanning,
respiratory-controlled spiral scanning,
respiratory-controlled sequence,
CTA scan with at least one of
EKG-triggered sequence,
EKG-triggered spiral,
adaptive 4D spiral,
cardio shuttle, and
flash mode,
scanning with ultra high resolution,
dose power,
dose modulation, and
tube voltage.

7. The CT system as claimed in claim 3, wherein the CT system is configured to determine at least one scan parameter from the following list on the basis of previously specified patient parameters and examination parameters, and applied:
a type of the scan with at least one of,
single-source/dual-source,
single-energy/dual-energy,
continuous scanning,
respiratory-controlled spiral scanning,
respiratory-controlled sequence,
CTA scan with at least one of
EKG-triggered sequence,
EKG-triggered spiral,
adaptive 4D spiral,
cardio shuttle, and
flash mode,
scanning with ultra high resolution,
dose power,
dose modulation, and
tube voltage.

8. The CT system as claimed in claim 5, wherein the CT system is configured to determine at least one scan parameter from the following list on the basis of previously specified patient parameters and examination parameters, and applied:
   a type of the scan with at least one of,
      single-source/dual-source,
      single-energy/dual-energy,
      continuous scanning,
      respiratory-controlled spiral scanning,
      respiratory-controlled sequence,
      CTA scan with at least one of
         EKG-triggered sequence,
         EKG-triggered spiral,
         adaptive 4D spiral,
         cardio shuttle, and
         flash mode,
   scanning with ultra high resolution,
   dose power,
   dose modulation, and
   tube voltage.

9. A CT system for scanning a patient, comprising:
   a tube/detector system, settable by a control device in respect of at least one of tube voltage and dose power; and
   a computer system to control the CT system, the computer system including,
      an evaluation unit for a logical decision tree, integrated into the computer system, to determine examination and scan parameters for the CT system on the basis of input of at least one patient parameter described in a parameter list and to operate the CT system using the determined examination and scan parameters, wherein the evaluation unit is configured to make a decision based on the entered patient parameters as to whether a topogram is created and determine whether to utilize the topogram as a further patient parameter.

10. The CT system as claimed in claim 9, wherein the parameter list contains at least one of the following patient parameters:
   an organ to be examined,
   a clinical question,
   individual characteristics of the patient,
   laboratory values of the patient, and
   physiological values of the patient.

11. The CT system as claimed in claim 10, wherein the CT system is configured to determine at least one examination parameter from the following list on the basis of previously specified patient parameters, and signaled:
   a position the patient is in,
   a necessity and medical possibility of a contrast-agent application,
   a necessity of applying an EKG, and
   a necessity of measuring the respiration.

12. The CT system as claimed in claim 10, wherein the CT system is configured to determine at least one scan parameter from the following list on the basis of previously specified patient parameters and examination parameters, and applied:
   a type of the scan with at least one of,
      single-source/dual-source,
      single-energy/dual-energy,
      continuous scanning,
      respiratory-controlled spiral scanning,
      respiratory-controlled sequence,
      CTA scan with at least one of
         EKG-triggered sequence,
         EKG-triggered spiral,
         adaptive 4D spiral,
         cardio shuttle, and
         flash mode,
   scanning with ultra high resolution,
   dose power,
   dose modulation, and
   tube voltage.

* * * * *